United States Patent

Feldman et al.

[11] Patent Number: 5,225,979
[45] Date of Patent: Jul. 6, 1993

[54] METHOD AND SYSTEM FOR CALIBRATING AN X-RAY SCANNER FROM THE IMAGE OF AT LEAST ONE CALIBRATION STANDARD

[75] Inventors: Andréi Feldman, Paris; Dominique Cornuejols, Palaiseau, both of France

[73] Assignee: General Electric CGT SA, Issy les Moulineaux, France

[21] Appl. No.: 884,453

[22] Filed: May 14, 1992

Related U.S. Application Data

[63] Continuation of Ser. No. 426,158, Oct. 25, 1989, abandoned.

[30] Foreign Application Priority Data

Oct. 28, 1988 [FR] France ................................. 88 14166

[51] Int. Cl.$^5$ ............................................. G06F 15/00
[52] U.S. Cl. .................................. 364/413.13; 378/207; 250/252.1
[58] Field of Search .................... 364/413.13; 378/207; 250/252.1 R

[56] References Cited

U.S. PATENT DOCUMENTS

| | | | |
|---|---|---|---|
| 4,035,651 | 6/1977 | LeMay | 364/413.15 |
| 4,352,020 | 9/1982 | Horiba et al. | 378/18 |
| 4,789,930 | 12/1988 | Sones et al. | 364/413.13 |

FOREIGN PATENT DOCUMENTS

| | | |
|---|---|---|
| 89096 | 9/1983 | European Pat. Off. . |
| 154429 | 9/1985 | European Pat. Off. . |
| 218367 | 4/1987 | European Pat. Off. . |
| 2368760 | 5/1978 | France . |

Primary Examiner—Roy N. Envall, Jr.
Assistant Examiner—Laura Brutman
Attorney, Agent, or Firm—Nilles & Nilles

[57] ABSTRACT

A method and a system for calibrating an x-ray scanner, in which the lengths $d_{ij}$ of x-ray paths are first computed by means of the image of the calibration standard. There are then computed both the theoretical attenuations $Ac_{ij}$ and the attenuations $Am_{ij}$ measured on the image. There are then deduced the coefficient of proportionality K between the values $Ac_{ij}$ and $Am_{ij}$ in order to obtain values of $K \times Ac_i$. The values $KAc_i$ and $Am_i$ are employed for calculating the corrections to be made per channel as a function of the attenuation.

14 Claims, 4 Drawing Sheets

METHOD AND SYSTEM FOR CALIBRATING AN X-RAY SCANNER FROM THE IMAGE OF AT LEAST ONE CALIBRATION STANDARD

This application is a continuation of application Ser. No. 07/426,158, filed on Oct. 25, 1989, now abandoned.

BACKGROUND OF THE INVENTION

1. Field of the Invention

This invention relates to x-ray scanners and more particularly to a method for calibrating devices of this type which utilizes the image of one or a number of calibration standards. The invention is also concerned with a system for carrying out said method.

2. Description of the Prior Art

In order to examine a patient, it is becoming an increasingly common practice to employ x-ray devices known as scanners which produce images of cross-sections of the patient's body. These devices are based on the physical phenomenon of absorption of x-rays by the human body. This absorption is directly related to the distance x of travel of the x-rays within the body in accordance with the formula:

$$I = I_o e^{-bx}$$

where:

$I_o$ is the intensity of the radiation which enters the human body,

I is the intensity of radiation which passes out of the human body, b is a coefficient of attenuation which depends on the body through which the radiation passes.

In a logarithmic measurement scale, the attenuation $I/I_o$ is equal to bx or in other words proportional to the distance x.

As shown in FIG. 1, a scanner is essentially constituted by an x-ray source 10 associated with a detection device 11, these two elements being disposed in a fixed geometrical relationship to each other in order that the body to be examined may be positioned between them. Furthermore, they are supported by a structure (not shown) which is capable of rotating about the body to be examined so as to irradiate the body at different angles. The x-ray source, which is controlled by a device 13, emits x-rays in an angular sector which has a sufficient width to illuminate the entire cross-section of the body. The detection device 11 has the shape of an annular sector, the length of which is adapted to the width of the x-ray beam and is constituted by a large number of elementary detectors 12 in juxtaposed relation to each other.

In order to obtain an image of the cross-section of the human body through which the x-ray beam passes, the structure which supports the source 10 and the detection device 11 is caused to rotate about the body and output signals of the elementary detectors 12 are measured and then suitably processed in accordance with known methods in order to obtain a representative image of the cross-section. For this processing operation, the elementary detectors 12 (also known as channels) are connected to an electronic device 14 which carries out in the first place a computation of the logarithm of the signals received so as to obtain a signal whose amplitude is proportional to the attenuation of the x-rays.

As a result of different phenomena which will not be explained here, the amplitude of said signal in the case of each elementary detector or channel is not proportional to the attenuation which has in fact been sustained. In consequence, in order to overcome this disadvantage, various methods have been devised which consist for example in recording the output signals of the channels in the presence of bodies having known dimensions and a known coefficient of absorption so as to compute the attenuations (calculations of logarithms) and to compare these measured attenuations with values computed as a function of the dimensions and of the absorption coefficient of the body or calibration standard. These comparisons make it possible to deduce a law of correspondence or a modifying law between the measured values and the values which should be obtained. This law can be in the form of correspondence files or of mathematical formulae representing this correspondence in respect of each detection channel.

The standards employed for carrying out these so-called calibration measurements are for example blocks of different thicknesses which are introduced in proximity to the x-ray source, thus entailing the need for handling operations at the level of the source in order to introduce and withdraw these blocks. Furthermore, the shapes of said blocks and their positions are remote from the shape and position of the body of the patient to be examined, thus increasing the nonlinearity of the system.

In U.S. Pat. No. 4,352,020, it is proposed to use circular blocks 15, 16 and 17 having different diameters which are placed at the center of rotation of the support structure. This makes it possible to come closer to the conditions of measurements to be performed on the body to be examined. This patent also proposes to make use of a cone-shaped standard having a circular cross-section which is displaced transversely with respect to the beam so as to obtain different attenuation lengths. With the standards described, the measurements are performed with respect to a predetermined position of the support structure and in the case of each standard.

FIG. 2 shows the shape of three response curves 20, 21 and 22 of the attenuation as a function of the position of the channels in the case of measurements on three standards of circular shape. The measured values are represented by the dots and vary about a mean value which represents the theoretical value in a linear system. These curves can be employed as follows: when the measured signal corresponds to a point A, it will be deduced from this that the linear signal is the point A' of the mean curve 20. When the measured signal corresponds to a point B located between the curves 20 and 21, the linear signal will be deduced therefrom by interpolation between the curves 20 and 21. This interpolation can be computed in accordance with a linear law or more generally a polynomial law.

The curves 23 and 24 of FIG. 3 show in another form the principle of calibration at the level of a channel. These curves describe, in a given channel, the attenuation as a function of the thickness x of measured values (curve 23) and in respect of computed values (straight line 24). In fact, the measured values produce points which are connected to each other in accordance with a predetermined law which may be linear or polynomial so as to obtain a continuous curve. When an attenuation is measured, this corresponds for example to point C of curve 23 and the linear value corresponding to the point C' of curve 24 is deduced therefrom.

The U.S. patent cited earlier describes an apparatus in which the correspondence between the measured values and the real values of attenuation is established by means of a system of files created during the calibration operation. In regard to interpolation, the patent proposes linear, cubic and biquadratic interpolations, but the linear interpolation is alone described in detail.

The methods of calibration which have been briefly described in the foregoing are distinguished by the fact that they carry out a processing operation on the measured signals in order to obtain an image which is free from artifacts or in other words without flaws. However, it is not always easy to obtain an image of this quality, especially on account of the fact that the calculations are made with certain approximations which can be very rough in some instances.

In consequence, one object of the present invention is to carry out a method which processes, not the measured signals themselves, but the image obtained so as to eliminate circular artifacts.

Another object of the present invention is to provide a system which makes it possible to carry out said method.

SUMMARY OF THE INVENTION

The invention relates to a method of calibration of an x-ray scanner which comprises an x-radiation source and an N-channel detection device, said method being distinguished by the fact that it involves the following operations:

positioning of a first circular calibration standard between the x-radiation source (30) and the detection device (31), performance of one scanner revolution corresponding to m separate views, reconstruction of the image (81) of the calibration standard (32) so as to obtain a matrix image which indicates the value of brightness of the elementary image point or pixel in respect of each point of coordinates x and y, computation, by means of the matrix image, of the $N \times m$ lengths $d_{ij}$ of the x-ray paths in respect of the N channels and the m views, computation of the theoretical and fictitious attenuations $AC_{ij}$ at the level of the image in respect of the paths $d_{ij}$ on the assumption that the brightness has a fixed and uniform value in the case of each pixel, measurement by means of the matrix image, of the attenuations $Am_{ij}$ in the case of the same paths $d_{ij}$ while taking into account the real values of brightness of the pixels, computation in the case of each channel, of the mean values of the attenuations $Ac_i$ and $Am_i$, computation of a coefficient of proportionality K between the values $Ac_i$ and $Am_i$, so that $$K \sum_{i=1}^{N} Ac_i = \sum_{i=1}^{N} Am_i$$

computation of the attenuations $KAc_i$, computation, from the values $KAc_i$ and $Am_i$, of the corrections to be applied to each channel as a function of the attenuation.

The invention also relates to a system for carrying out the method, said system being distinguished by the fact that it comprises:

means for producing a matrix image of the calibration standard in the form of coordinates x and y of pixels and of values of brightness of said pixels, first computation means for calculating from the matrix image of the calibration standard $N \times m$ lengths $d_{ij}$ of the x-ray paths in respect of the N channels and the m views, as well as the values $Ac_{ij}$, second computation means for calculating the values of attenuation $Am_{ij}$ in respect of the lengths $d_{ij}$, third computation means for calculating on the one hand the coefficient of proportionality K between the values $Ac_i$ and $Am_i$ and, on the other hand, the values $K \times Ac_i$, recording means for recording the values $K \times Ac_i$ and $Am_i$, means for computing, from values $K \times Ac_i$ and $Am_i$, the corrections to be made in the case of each channel as a function of the attenuation.

DETAILED DESCRIPTION OF THE INVENTION

Figure 1:
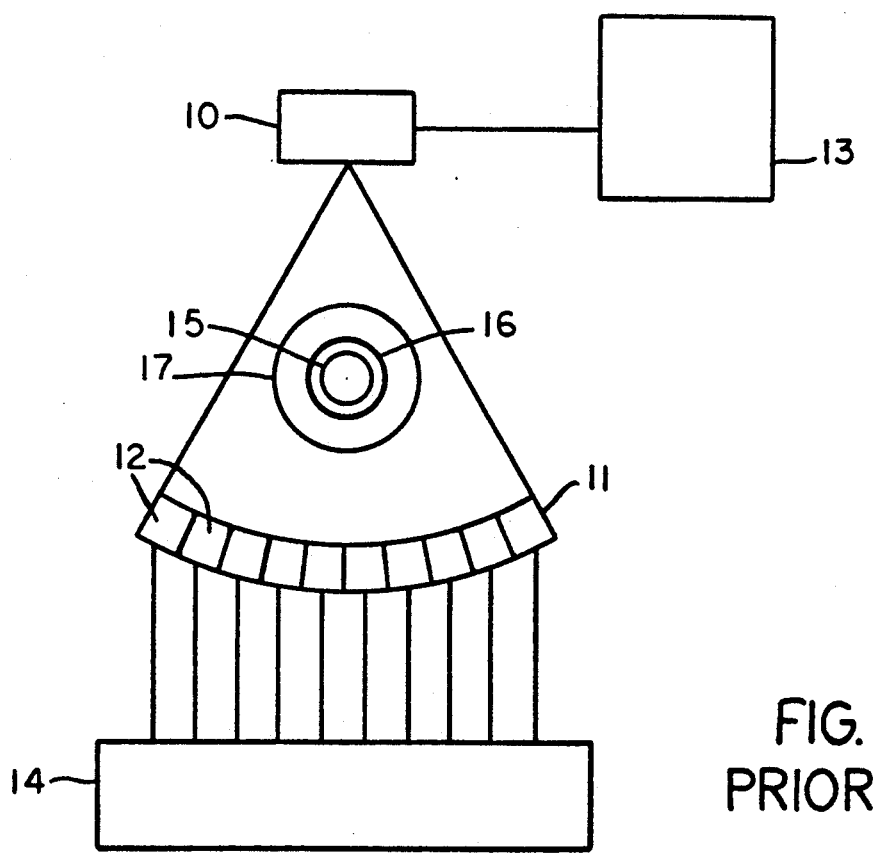
FIG. 1 is a schematic diagram of an x-ray scanner in which calibration is obtained by means of circular standards.
Figure 2:
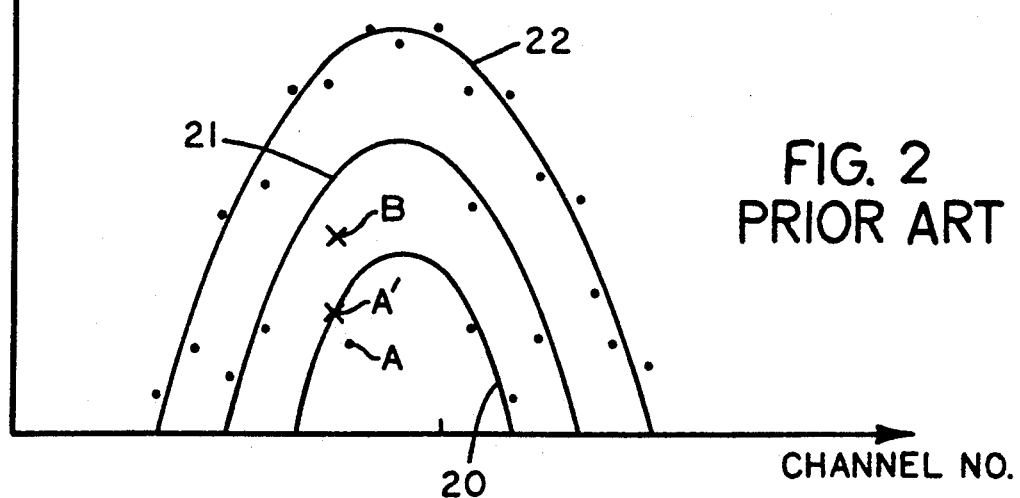
FIG. 2 is a diagram showing different curves of attenuation as a function of the position of the detectors or channels and of the diameter of the calibration standard.
Figure 3:
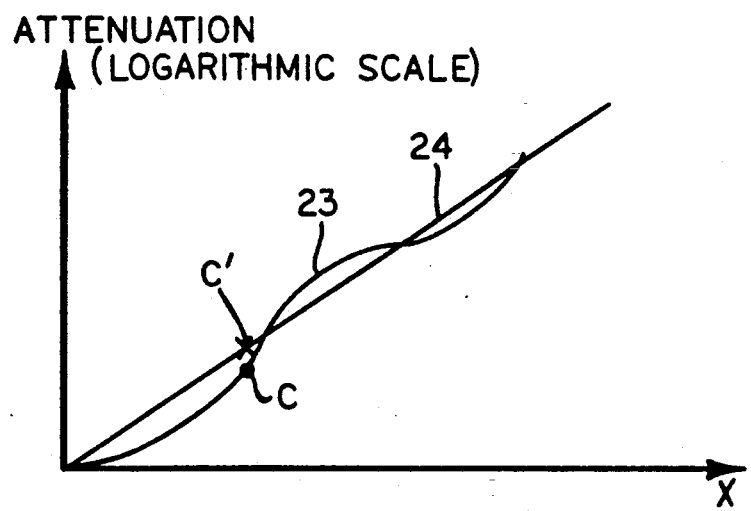
FIG. 3 is a diagram showing the curves of theoretical and measured attenuation in the case of a predetermined detector or channel.

FIGS. 1, 2 and 3 which have served to describe the prior art in the introductory part of this specification will not be described again.

As already mentioned earlier, the method in accordance with the invention carries out the calibrating operation by utilizing the image of the standard as obtained by the scanner. The image corresponds to measured values of the attenuation containing defects and is employed for computing theoretical values of attenuation which are compared with the measured values in order to obtain values of correction for the measured values. In other words, the image of the calibration standard is corrected by computation in order to remove its defects. The corrections thus computed will be those subsequently employed for modifying the measured values on a patient. In order to obtain corrections according to the length of path of the x-rays within the patient's body, it is necessary to calculate the corrections for calibration standards having different diameters.

Figure 4:
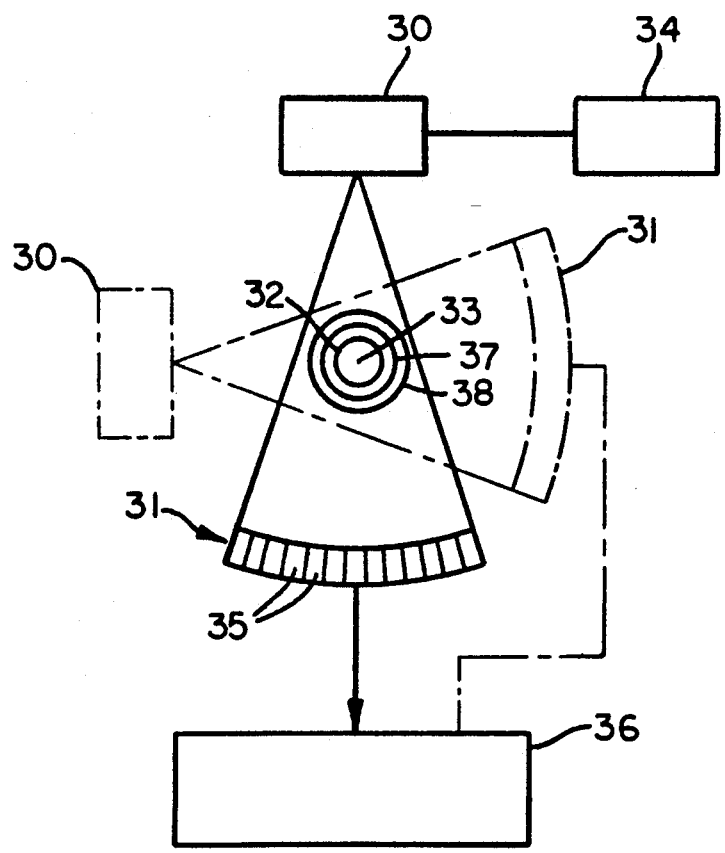
FIG. 4 is a schematic diagram of an x-ray scanner which shows two positions of the scanner about a circular calibration standard.

The diagram of FIG. 4 is similar to that of FIG. 1 in the sense that it shows an x-ray scanner which includes an x-ray source 30 and a detection device 31 comprising N detectors or channels 35, a patient's body being interposed between the source and the detector array under normal operating conditions or a standard 32 of circular shape being interposed at the time of calibrating operations. Although not shown in the drawings, a structure is provided for supporting the source 30 and the device 31 and causing the entire assembly to rotate around the patient's body or the calibration standard, the axis of rotation being materialized by the point 33. In the majority of calibration methods of the prior art, the center of the circular standard must coincide with the axis of rotation 33. This condition is not necessary in the method according to the invention. The x-ray source is controlled by a control device 34 whilst the different detectors or channels 35 of the device 31 are connected to an electronic system 36 which will be described with reference to FIG. 6. Moreover, means (not shown) are provided for producing rotational displacement of the assembly consisting of source 30 and detector 31 so that said assembly can take up a certain number m of predetermined angular positions $\alpha_j$, as it rotates as illustrated in FIG. 4. In the remainder of the description, the term "view" will designate all of the N signals collected from the N detectors of the detection device 31 in respect of an angular position $\alpha_j$. By way of example, $\alpha_j$ corresponds to the angular inclination with respect to the horizontal plane which passes through the point 33.

The method of calibration in accordance with the invention first of all consists in obtaining a series of m views $V_1 \ldots V_j \ldots V_m$ without any calibration standard, this operation being known as "acquisition in the air". These views serve as a reference for measuring the attenuations when the calibration standard or the patient's body is in position. This first operation will be more readily understood by referring to the block diagram of FIG. 6. The signals delivered by the N detectors or channels $C_1 \ldots C_i \ldots C_N$ are applied to an analog/digital coding circuit 50 which delivers digital values. These digital values will be used to carry out all the operations which will be described hereinafter. These operations can be performed by a suitably programmed computer.

The N digital values resulting from a measurement at an elementary angular position $\alpha_j$ or view are applied to a logarithm computation circuit 51. The logarithmic values are subtracted in a circuit 52 from a logarithmic reference value REF delivered by a detector or so-called monitor which receives the x-radiation directly without attenuation irrespective of the angular position $\alpha_j$. These N differential values, which correspond in each case to one channel, give the values of acquisition in the air in the case of one view. These N values are recorded in the memory 54 at the time of the acquisition operation by means of the direct connection 70. This operation is repeated for each of the m views and the value obtained for each channel is added to the preceding values and averaged in order to obtain a mean value which replaces in the memory 54 the mean value which results from the preceding views. After m views, the memory 54 contains N mean values, namely one per channel, which serve as a reference during the other calibration operations and during the operations of measurement on a patient.

When this first operation of acquisition in the air (which is already known) has been performed, a first circular calibration standard 32 is placed in position and one carries out a series of m views and the signals corresponding to each view are processed in the following manner. After processing in the circuits 50, 51 and 52 as explained earlier, the N digital values of a view are applied to a second subtraction circuit 53 in which they are subtracted from the N digital values of the mean value without standard which are contained in the memory 54. By means of this subtraction, one is free from the characteristics of the detectors 35 which are different from one detector to another. It will be observed that the first subtraction in the circuit 52 makes it possible to be free in particular from variations in emission of the source 30.

The N×m codes supplied by the second subtraction circuit 53 are delivered to an image reconstruction device 55 which, in accordance with a known method, produces an image which is representative of the circular standard 32 which is placed in position at the time of calibration or of a cross-section of the patient's body at the time of normal operation of the scanner. This image may, for example, be displayed by means of a screen 57 consisting for example of a matrix of elementary points or pixels arranged in rows and columns. The image is recorded in an image memory 56 in the form of a system of coordinates x and y of the pixels, there being associated with each coordinate a value of brightness of the pixel in accordance with a predetermined scale.

This representative image of the circular calibration standard 32 presents artifacts resulting from non-linearities of the system. The corrections in accordance with the method of the invention are calculated from the images of several calibration standards.

Figure 7:
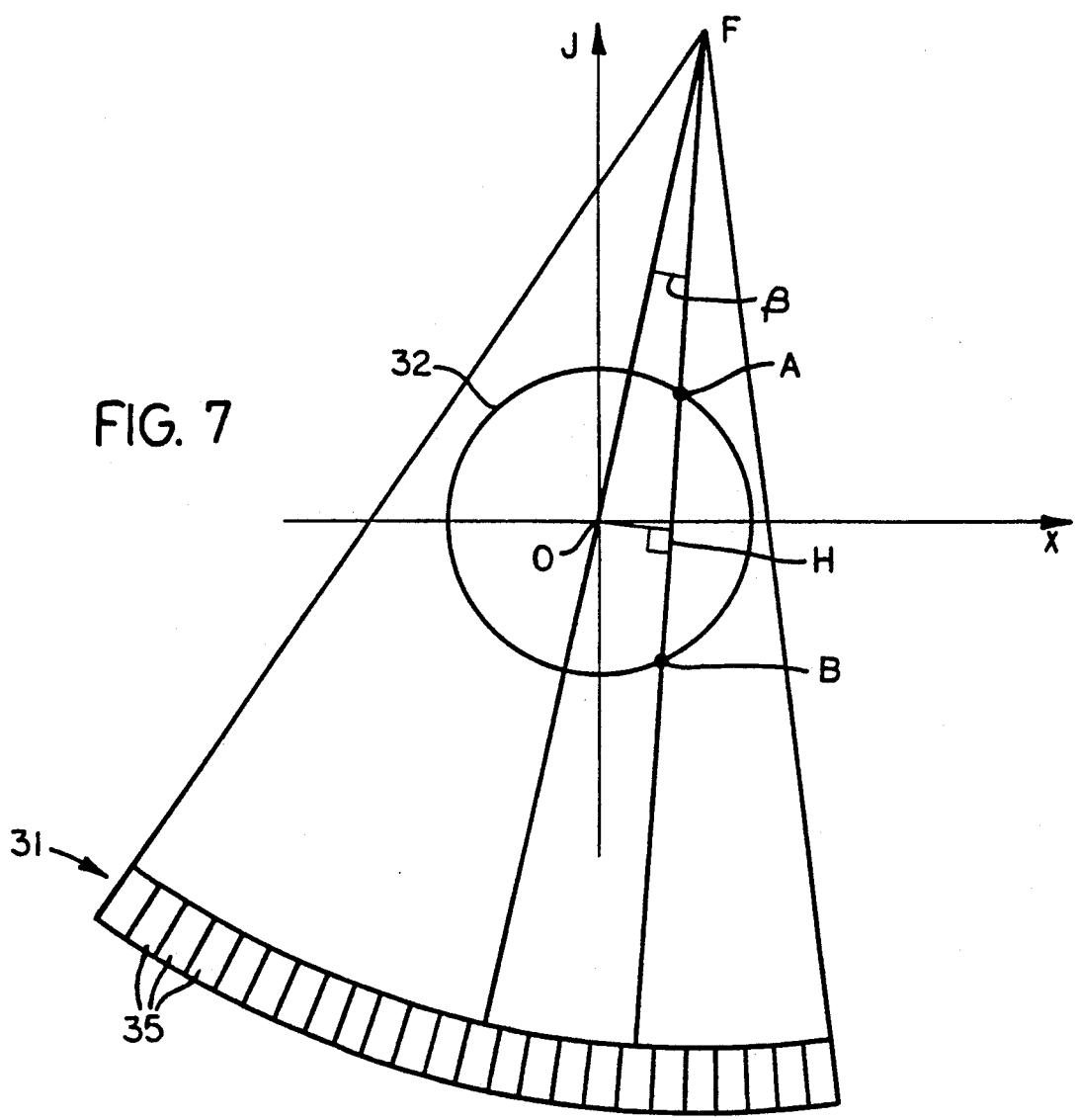
FIG. 7 is a geometrical drawing showing the relative positions of the calibration standard with respect to the scanner.
Figure 5:
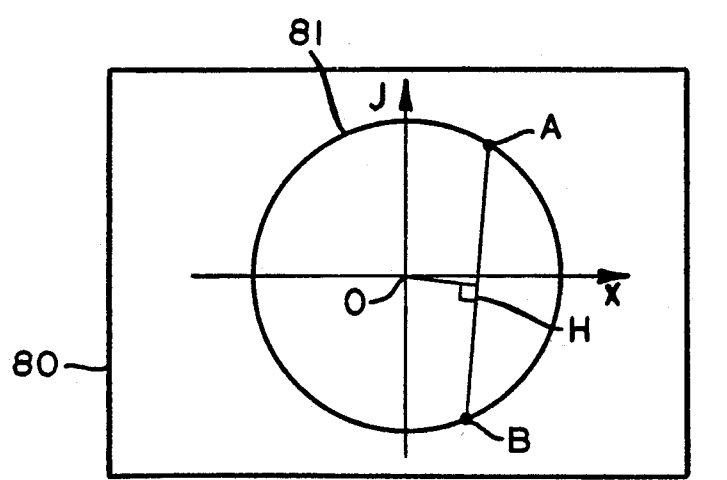
FIG. 5 is a geometrical diagram showing the image of a circular standard on a visual display device.

In FIGS. 5 and 7, the segment AB represents a path of an x-ray through the calibration standard 32. The principle of the method and of the system in accordance with the invention is accordingly as follows. The length AB is measured by means of the coordinates x and y of A and of B. Since consideration is given to a path within a calibration standard in which the absorption is fixed and uniform, there is computed the theoretical and fictitious attenuation Ac to which the x-radiation is subjected on the geometrical path AB. Moreover, one measures the measured attenuation Am by means of the values of brightness of the pixels on the path AB as recorded in the memory 56. In the absence of artifacts, these two attenuations Ac and Am must be equal to within a factor K which does not depend on AB, if they are not equal, a correction must be made. Determination of this correction is effected in the case of each channel 35. To this end, the attenuations Ac and Am are respectively computed for different orientations of the segment AB corresponding to one and the same distance OH and each orientation in turn corresponds to a predetermined angular position of the scanner, that is to say a view.

It is worthy of note that, by virtue of the geometrical design of the scanner, the radiation on the different paths AB at the same distance OH=d is always detected by the same channel. As a corollary, in the case of another distance OH, the segment AB will have a different length and the radiation will be detected by another channel. In other words, each channel will correspond to a certain distance OH which is determined by the following trigonometric relation (FIG. 7)

$$OH = OF \sin \beta$$

knowing that, from one channel to the next, the angle $\beta$ varies by a fixed value $\theta$ in accordance with the design of the scanner. These remarks lead one to consider only the paths AB which correspond to distances OH associated with an angle $\beta$ relating to a predetermined channel, which means that N paths AB are considered when there are N channels.

When making use of a single calibration standard, only one correction per channel can be determined, which is insufficient. Accordingly, the invention proposes a method in which a plurality of circular calibration standards are employed, thus making it possible to determine a corresponding number of corrections per channel as a function of the length of the path AB.

Figure 6:
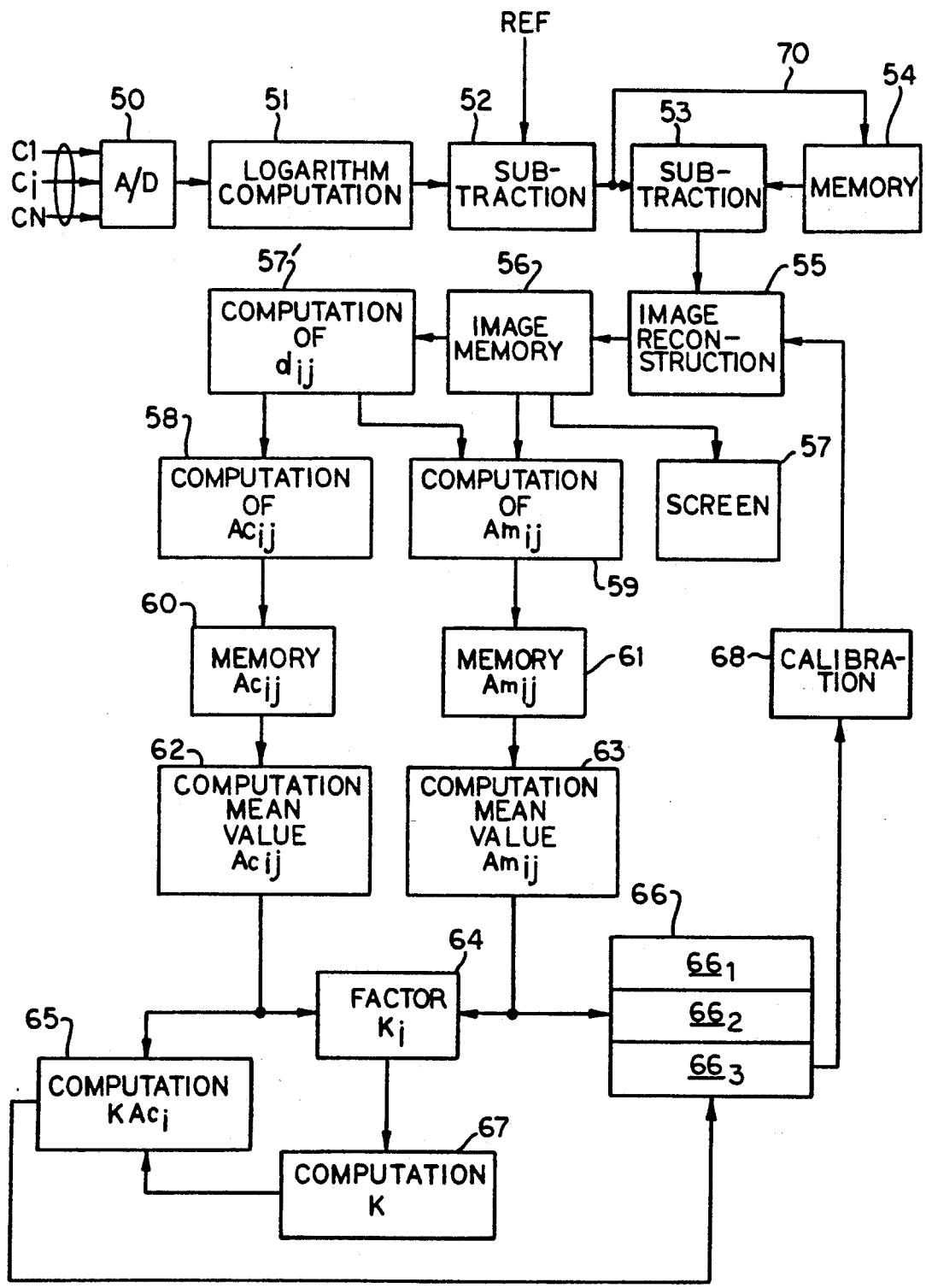
FIG. 6 is a functional diagram of a system for processing read signals in order to carry out the method of calibration in accordance with the invention.

The principles of correction in accordance with the invention having thus been set forth, their practical application will be more readily apparent from the following description of the other elements which have not yet been described, reference being made to the diagram of FIG. 6.

The data contained in the image memory 56 are processed in the devices 57' to 68 as follows. First of all, the device 57' carries out the operation of computation of the paths AB=d on the image as a function on the one hand of the distance OH, this latter being subject to variation as a function of the angular pitch $\theta$ between two consecutive channels and, on the other hand, of the orientation corresponding to an angular position $\alpha_j$ of the scanner or in other words to a view ($\alpha_j$ is the angle between the half-lines OF and Ox in FIG. 7). It is understood that the result of this calculation can be in the form of a file which indicates in respect of each angle $\alpha_j$ the paths AB corresponding to each channel $C_i$. This file therefore contains $N \times m$ values $d_{ij}$.

The contents of said file serve to compute the theoretical and fictitious attenuations (Ac) and measured attenuations (Am) referred-to in the foregoing, in respect of each path AB.

Computation of Ac follows directly from the file of the values $d_{ij}$ by multiplying these latter by the coefficient of absorption of the theoretical calibration standard 32 expressed in Housfield units, in a circuit 58. There are thus obtained $N \times m$ theoretical and fictitious values $Ac_{ij}$ which constitute measurements of the attenuation. These values are recorded in a memory 60 which is organized in rows and columns, each row being intended to correspond to one view (angle $\alpha_j$) and each column being intended to correspond to a channel $C_i$.

Computation of Am is carried out in a circuit 59 by means of the file of paths $d_{ij}$ and of pixel brightness data contained in the image memory 56. More precisely, the pixels which establish each path $d_{ij}$ are determined and the sum of brightnesses of these pixels is calculated, which constitutes a measurement of the attenuation $Am_{ij}$. The $N \times m$ values $Am_{ij}$ are recorded in a memory 61 which is organized in the same manner as the memory 60.

As has been mentioned earlier, when no defect is present, the values $Ac_{ij}$ and $Am_{ij}$ should be equal in pairs to within a proportionality factor K. The differences between these values, after introduction of the proportionality factor, are therefore a measurement of the corrections to be made on the measurements in order to remove defects.

Said proportionality factor K is determined by means of the contents of the memories 60 and 61. To this end, the arithmetical mean of the values contained in each column of the memory 60 is determined in a circuit 62 in order to obtain N values $Ac_i$ and the same procedure is adopted in a circuit 63 in order to obtain N mean values $Am_i$ of the values contained in each column of the memory 61. The mean values are then compared in pairs in a circuit 64 in order to obtain N proportionality factors $K_i$ such that:

$$K_i = \frac{Am_i}{Ac_i}$$

Finally, the factor K is obtained by establishing the mean of the N values $K_i$ in a circuit 67. It is this factor K, which results from a general mean, which is employed in a circuit 65 for modifying the mean values $Ac_i$ and obtaining the values $K \times Ac_i$ which are comparable with the mean values $Am_i$. The mean values $KAc_i$ and $Am_i$ are recorded in a memory 66. There is thus obtained for each channel a correspondence between a measured value $Am_i$ and a theoretical value $K \times Ac$; in respect of a given path $d_i$ in the circular calibration standard 32 corresponding to a channel $C_i$.

In the case of one and the same channel $C_i$, it is desirable to have other paths $d_i$ in order to introduce more accurate corrections. To this end, the operations described in the foregoing with reference to FIG. 6 are repeated with other circular calibration standards having different diameters. This makes it possible to record in the memory 66 other groups of pairs of correspondence values for each channel in the case of other paths $d_i$.

Thus, in the memory 66, the portion $66_1$ is assigned to the group of pairs of correspondence values obtained with the first calibration standard 32, the portion $66_2$ is assigned to the second standard 37 and the portion $66_3$ is assigned to the third standard 38.

The data contained in the memory 66 are employed in a circuit 68 for calibrating the machine, which means that these data will be employed for computing a correction of the attenuation.

The method of calibration in accordance with the invention therefore involves the following operations:

positioning of a first circular calibration standard 32 between the radiation source 30 and the detection device 31 comprising N detectors, performance of one scanner revolution corresponding to m separate and distinct views, reconstruction of the image of the calibration standard 32 in accordance with a conventional method so as to obtain a matrix image which indicates in respect of each point of coordinates x and y the value of brightness of the corresponding pixel, computation, by means of the matrix image, of the $N \times m$ lengths $d_{ij}$ of the x-ray paths in respect of the N channels and the m views, computation (circuit 58) of the theoretical and fictitious attenuations $Ac_{ij}$ in the case of the paths $d_{ij}$ and recording of said attenuations in a memory 60, computation (circuit 59) by means of the matrix image of the measured attenuations $Am_{ij}$ in respect of the same paths $d_{ij}$ while taking into account the values of brightness of the pixels, and recording of said attenuations in a memory 61, computation (circuits 62 and 63) for each channel, of the mean values $Ac_i$ and $Am_i$ of the attenuations $Ac_{ij}$ and $Am_{ij}$, computation (circuits 64 and 67) of a coefficient of proportionality K between the values $Ac_i$ and $Am_i$, computation of the attenuations $K \times Ac_i$ (circuit 65) and recording of said attenuations in a memory $66_1$ which also records the corresponding attenuations $Am_i$, reiteration of the above operations after positioning of a second circular calibration standard and recording of the attenuations $K \times Ac_i$ and $Am_i$ in a memory $66_2$ and so on for other calibration standards, calibration (circuit 68) from the attenuations $KAc_i$ and $Am_i$.

The invention has been described on the assumption that the circular calibration standards were centered on the axis 33 of rotation of the scanner. However, this centering operation is not necessary since the operations performed on the basis of the matrix image are independent of the respective positions of the centers of the standard and of the scanner.

The invention has been described mainly with reference to the diagram of FIG. 6 but it is clear that the operations and functions described can be performed in accordance with a system having a different functional diagram without thereby departing from the scope of the present invention.

What is claimed is:

1. A method of calibrating an x-ray scanner which comprises an x-radiation source and an N-channel detection device, wherein said method comprises the following steps:

positioning a first circular calibration standard between the x-radiation source and the detection device, performing one scanner revolution corresponding to m separate and distinct views, collecting x-ray attenuation data in each of the N channels for each of the m views, calculating measured attenuations $Am_{ij}$ corresponding to x-ray paths $d_{ij}$ of x-rays, based upon the x-ray attenuation data, wherein i runs from 1 to m corresponding to the m views, and j runs from 1 to N corresponding to the N detectors, computing theoretical attenuations $Ac_{ij}$, for the standard based upon the position, shape, and density of the standard, and a model of x-ray absorption, along paths $d_{ij}$, computing mean values $Ac_i$, of attenuations $Ac_{ij}$, by averaging all the values $Ac_{i1}, Ac_{i2} \ldots Ac_{im}$ corresponding to the m views for the ith detector, computing mean values $Am_i$, of attenuations $Am_{ij}$, by averaging all the values $Am_{i1}, Am_{i2} \ldots Am_{im}$, corresponding to the m views for the ith detector, computing a coefficient of proportionality K between the mean values of $Ac_i$ and $Am_i$, for i=1 to N, computing attenuations $K \times Ac_i$, determining, from the values $K \times Ac_i$ and $Am_i$, corrections to be applied to each channel as a function of the attenuation, and calibrating the scanner using the corrections determined from the values $K \times Ac_i$ and $Am_i$.

2. A method of calibration according to claim 1, wherein at least some of the operations are repeated for other calibration standards having different diameters.

3. A method of calibration according to claim 1, wherein the step of computing the coefficient of proportionality K includes a first step of computing the mean of the values of both Aci and Ami corresponding to a the ith channel, a second step of comparing the mean values thus obtained so as to obtain one coefficient of proportionality $K_i$ per channel and a third step of computing the mean value of the coefficients $K_i$, K being the mean value of the coefficients K.

4. An x-ray scanner system, comprising:
   an x-radiation source,
   a N-channel detection device for detecting x-rays from said x-radiation source,
   a calibration standard interposed between the x-ray radiation source and the N-channel detection device,
   means for producing a measured attenuation matrix $Ac_{ij}$, wherein i=1 to N, and i corresponds to the ith channel of the N channels of the detector, j=1 to m, and j corresponds to the jth view of m views of the calibration, said measured attenuation matrix containing x-ray attenuation values due to transmission of x-rays through the calibration standard,
   first computing means for calculating, from the attenuation matrix of the calibration standard, N=m lengths $d_{ij}$ of x-ray paths through the standard,
   means for determining a theoretical attenuation matrix $Am_{ij}$ corresponding to theoretical attenuation of x-rays passing through the calibration standard based upon the position, shape and density of the standard, and a model of x-ray attenuation, for m views and N channels,
   second computing means for calculating a coefficient of proportionality K between the values $Ac_{ij}$ and $Am_{ij}$, by summing both $Ac_{ij}$ and $Am_{ij}$ over i and j and setting K equal to a ratio of the sums,
   recording means for recording the values $K \times Ac_i$ and the values $Am_i$, wherein $Ac_i$ and $Am_i$ are the means values corresponding to the m views for each of the i detectors,
   third computing means for calculating, from the values $K \times Ac_i$ and $Am_i$, corrections to be applied to each channel as a function of the attenuation, and
   means for calibrating the x-ray scanner system using the corrections calculated from $K \times Ac_i$ and $Am_i$.

5. A method of calibrating an x-ray scanner which includes a source of x-radiation and a detection device having multiple channels, said method comprising the steps of:
   (A) collecting x-ray attenuation data for each channel for a first calibration standard disposed between said source of x-radiation and said detection device; then
   (B) computing, from said x-ray attenuation data, theoretical attenuations and measured attenuations for each channel; then
   (C) computing a coefficient of proportionality between said theoretical attenuations and said measured attenuations; then
   (D) determining values of corrections to be applied to each channel, using said coefficient of proportionality, said theoretical attenuations, and said measured attenuations; and then
   (E) calibrating said scanner, using the values of corrections determined in said step (D).

6. A method according to claim 5, wherein said step (A) comprises
   (i) collecting reference data for each channel using said source of x-radiation and said detection device, then
   (ii) positioning said first calibration standard between said source of x-radiation and said detection device, then
   (iii) collecting calibration data for each channel, using said source of x-radiation and said detection device, and then
   (iv) combining said reference data with said calibration data to obtain said x-ray attenuation data.

7. A method according to claim 6, further comprising repeating said steps (A) through (D) for a second calibration standard prior to said step (E), said second calibration standard having a diameter which is different than that of said first calibration standard.

8. A method according to claim 5, further comprising revolving said scanner around said calibration standard and obtaining a plurality of views, and wherein said step (A) comprises collecting x-ray attenuation data for each of said views.

9. A method according to claim 5, further comprising the step of displaying an image of said calibration standard.

10. A method according to claim 5, wherein said step (B) comprises computing said theoretical attenuations based upon the position, shape, and density of said first calibration standard.

11. An apparatus comprising:
(A) an x-ray scanner which includes a source of x-radiation and a detection device having multiple channels;
(B) a first calibration standard positioned between said source of x-radiation and said detection device; and
(C) means for calibration said x-ray scanner, said means for calibrating including
  (i) means for collecting for each channel, x-ray attenuation data for said first calibration standard,
  (ii) means for computing theoretical attenuations and measured attenuations for each channel, using said x-ray attenuation data,
  (iii) means for computing a coefficient of proportionality between said theoretical attenuations and said measured attenuations,
  (iv) means for determining values of corrections to be applied to each channel, using said coefficient of proportionality, said theoretical attenuations, and said measured attenuations, and
  (v) means for calibrating said scanner, using the values of corrections determined by said means (iv).

12. An apparatus according to claim 11, wherein said means (i) comprises
  (1) means for collecting reference data for each channel using said source of x-radiation and said detection device,
  (2) means for positioning said first calibration standard between said source of x-radiation and said detection device,
  (3) means for collecting calibration data for each channel using said source of x-radiation and said detection device, and
  (4) means for combining said reference data with said calibration data to obtain said x-ray attenuation data.

13. An apparatus according to claim 11, further comprising a display device which displays an image of said calibration standard.

14. An apparatus according to claim 11, wherein said means (ii) comprises means for computing said theoretical attenuations based upon the position, shape, and density of said first calibration standard.

* * * * *